US010231999B2

(12) United States Patent
Lee et al.

(10) Patent No.: US 10,231,999 B2
(45) Date of Patent: Mar. 19, 2019

(54) PROCESS FOR PREPARING CHOLINERGIC NEURONS

(71) Applicant: Korea Research Institute of Bioscience and Biotechnology, Daejeon (KR)

(72) Inventors: Sang Chul Lee, Daejeon (KR); Baek Soo Han, Daejeon (KR); Kwang-Hee Bae, Daejeon (KR); Hyejin Kim, Daejeon (KR); Won Kon Kim, Daejeon (KR); Kyoung Jin Oh, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 15/506,216

(22) PCT Filed: Aug. 13, 2015

(86) PCT No.: PCT/KR2015/008481
§ 371 (c)(1),
(2) Date: Feb. 23, 2017

(87) PCT Pub. No.: WO2016/032151
PCT Pub. Date: Mar. 3, 2016

(65) Prior Publication Data
US 2017/0266235 A1    Sep. 21, 2017

(30) Foreign Application Priority Data

Aug. 25, 2014   (KR) ........................ 10-2014-0110566

(51) Int. Cl.
*A61K 35/30*    (2015.01)
*C12N 5/0793*    (2010.01)
(Continued)

(52) U.S. Cl.
CPC .......... *A61K 35/30* (2013.01); *A61K 38/1787* (2013.01); *C12N 5/0607* (2013.01);
(Continued)

(58) Field of Classification Search
None
See application file for complete search history.

(56) References Cited

U.S. PATENT DOCUMENTS 8,796,022 B2    8/2014    Bissonnette et al.

FOREIGN PATENT DOCUMENTS

| KR | 10-0495532 B1 | 6/2005 |
|----|---------------|--------|
| KR | 10-0683199 B1 | 2/2007 |
| WO | WO 2004/015077 A2 | 2/2004 |
| WO | WO 2005/003320 A2 | 1/2005 |

OTHER PUBLICATIONS

Boulting, Gabriella L; et al; "A functionally characterized test set of human induced pluripotent stem cells" Nature Biotechnology, 29, 279-286, 2011 (Year: 2011).*

(Continued)

*Primary Examiner* — David W Berke-Schlessel
(74) *Attorney, Agent, or Firm* — John P. White; Cooper & Dunham LLP

(57) ABSTRACT

The present invention relates to a method for producing cholinergic neurons comprising obtaining neural progenitor cells from stem cells so as to continuously produce cholinergic neural cells with high purity and the same traits, followed by differentiating the neural progenitor cells into the cholinergic neurons, and cholinergic neurons produced therefrom. Since the method of preparing the cholinergic neurons provided in the present invention enables not only production of the cholinergic neurons with high purity, but also rapid production of the cholinergic neurons with the same traits, it can be widely used for effectively treating degenerative cranial nerve diseases such as Alzheimer's disease.

14 Claims, 5 Drawing Sheets

(51) Int. Cl.
  *C12N 5/10*  (2006.01)
  *A61K 38/17*  (2006.01)
  *C12N 5/074*  (2010.01)
  *A61K 45/00*  (2006.01)
  *A61K 48/00*  (2006.01)
  *C12N 5/00*  (2006.01)

(52) U.S. Cl.
  CPC ............ *C12N 5/0619* (2013.01); *C12N 5/10* (2013.01); *A61K 45/00* (2013.01); *A61K 48/00* (2013.01); *C12N 5/00* (2013.01); *C12N 2502/08* (2013.01)

(56) References Cited

OTHER PUBLICATIONS

Zhang, Su-Chun et al., "In vitro differentiation of transplantable neural precursors from human embryonic stem cells", nature biotechnology, vol. 19, Dec. 2001.

Gao, J. et al., "Human neural stem cell-derived cholinergic neurons innervate muscle in motoneuron deficient adult rats", Neuroscience 131, (2005), 257-262.

International Search Report in connection with PCT International Application No. PCT/ PCT/KR2015/008481.

Notice of Allowance dated Sep. 4, 2017 in connection with Korean Patent Application No. KR 10-2015-0119828 including English language machine translation.

Irene Faravelli, et al., "Motor neuron derivation from human embryonic and induced pluripotent stem cells: experimental approaches and clinical perspectives", Stem Cell Res. Ther., Jul. 14, 2014, 5(4):87.

Yoichiro Abe, et al., "Analysis of Neurons Created from Wild-Type and Alzheimer's Mutation Knock-In Embryonic Stem Cells by a Highly Efficient Differentiation Protocol", J. Neurosci., Sep. 17, 2003, 23(24):8513-25.

* cited by examiner

VAChT MAP2 DAPI

Tuj1 ChAT DAPI

GABA MAP2 DAPI

PROCESS FOR PREPARING CHOLINERGIC NEURONS

CROSS-REFERENCE TO RELATED APPLICATIONS

This application is a § 371 national stage of PCT International Application No. PCT/KR2015/008481, filed Aug. 13, 2015, claiming priority of Korean Patent Application No. KR 10-2014-0110566, filed Aug. 25, 2014, the content of each of which is hereby incorporated by reference into the application.

TECHNICAL FIELD

The present invention relates to a method for producing cholinergic neurons, more specifically to a method for producing cholinergic neurons comprising forming neural progenitor cells from stem cells, followed by differentiating the neural progenitor cells into cholinergic neurons so as to continuously produce cholinergic neurons with high purity and the same traits, and cholinergic neurons produced therefrom.

BACKGROUND ART

As mammal neurons do not regenerate if damaged, neurodegenerative diseases such as stroke, Parkinson's disease, or Alzheimer's disease may occur when the neurons are damaged. Accordingly, treatments that can cure diseases due to neuronal death have been actively studied worldwide for a long time, but an adequate treatment has not yet been developed.

Recently, research has been actively carried out to develop a method for treating the neurons damaged by differentiating stem cells, which are pluripotent cells capable of differentiating into various cells, into neurons. As the stein cells can be differentiated into various cells, such method may be fundamental in treating a disease that induces tissue damage. However, as it is not easy to obtain the stem cells or differentiate the stem cells into desired cells, and as the possibility of the stem cells themselves being rejected by patients' immune system can be problematic, the method has not been used universally. However, a cranial nerve disease accompanied by neural damage is considered to be the most appropriate object for the treatment using the stem cells because unlike other tissues, there is little rejection by the immune system in the cranial nervous system tissue, thereby making it possible to expect long-term survival of transplanted cells when the cells are transplanted from outside.

Studies for developing a method for applying the stein cells to treatments of diseases such as stroke, Alzheimer's disease, Parkinson's disease, demyelinating disease, and spinal cord injury are actively under way. For example, International Publication No. WO 2005/003320 discloses a method for inducing the stem cells into neurons, comprising sequentially adding and culturing a basic fibroblast growth factor (bFGF), fibroblast growth factor 8, sonic hedgehog (SHH), and brain-derived neurotrophic factor (BDNF) and ultimately co-culturing with astrocytes. Korean Patent Application No. 10-0495532 discloses a method for differentiating mesenchymal stem cells into neurons by culturing in a culture medium comprising an epidermal growth factor (EGF) and hepatocyte growth factor (HGF) and for proliferating the neurons.

Cholinergic neurons, a type of neuron, are located mainly in the basal forebrain and the hippocampus, having a form in which the neurons extend their axons to other parts of the brain including the cortex. It is known that the cholinergic neurons are directly involved in inducing nervous system diseases in the brain of animals, and that damage to the cholinergic neuron is accompanied by onset of various degenerative cranial nerve diseases such as Alzheimer's disease, Parkinson's disease, and amyotrophic lateral sclerosis. In particular, learning disabilities, one of the main symptoms of Alzheimer's disease, is predicted to be caused by damage to the cholinergic neurons.

In light of the above, research is actively underway on development of not only a method of using the cholinergic neurons as a therapeutic agent for various degenerative cranial nerve diseases, but also a method capable of differentiating the cholinergic neurons used for treating said diseases from the stem cells. According to what has been reported so far, the embryoid bodies are treated with bFGF, retinoic acid (RA), and SHH to differentiate into the cholinergic neurons. Specifically, the embryoid bodies form early neuroectodermal cells, and are posteriorized when treated with RA and differentiated into the cholinergic neurons when treated with SHH. Additionally, it is known that rat embryonic stem cells can be differentiated into the cholinergic neurons by co-culturing with murine bone marrow origin stromal feeder cells. A method for which the neural progenitor cells are cultured in a culture medium comprising SHH and RA and in a culture medium comprising bfGF and SHH, and in which the culture obtained therefrom is cultured in a culture medium comprising ascorbic acid (AA) and BDNF to differentiate into the cholinergic neurons, is known (Korean Patent Application No. 10-0683199).

However, the cholinergic neurons differentiated by the conventional method include other cells, in addition to pure cholinergic neurons, thereby causing a problem in that the cholinergic neurons cannot be directly used for treating neurodegenerative diseases, and this problem has not yet been resolved.

DISCLOSURE

Technical Problem

The present inventors have made diligent research efforts in order to develop a method for producing cholinergic neurons with high purity by differentiating stem cells. As a result, the present inventors have completed the present invention by confirming that rather than directly differentiating the stem cells into the cholinergic neurons, cholinergic neurons can be obtained with high purity by forming neural progenitor cells from the stem cells, followed by inhibiting proliferation of neurons other than the cholinergic neurons while differentiating the neural progenitor cells.

Technical Solution

An object of the present invention is to provide a method for producing cholinergic neurons comprising forming neural progenitor cells from stem cells, followed by differentiating the neural progenitor cells into cholinergic neurons. Another object of the present invention is to provide cholinergic neurons produced therefrom.

Advantageous Effects

Since the method for producing the cholinergic neurons provided in the present invention enables not only production of the cholinergic neurons with high purity, but also rapid production of the cholinergic neurons with the same traits, it can be widely used for effectively treating degenerative diseases such as Alzheimer's disease.

BEST MODE

Figure 1:
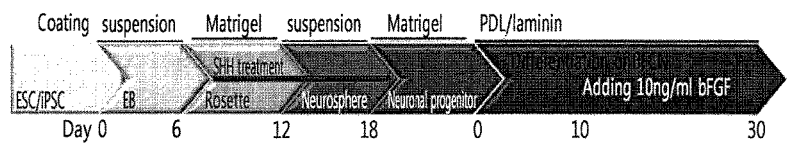
FIG. 1 is a flow chart showing the method for producing the cholinergic neurons of the present invention.

While conducting research in order to develop a method for producing the cholinergic neurons with high purity by differentiating the stem cells, the present inventors focused on a method via neural progenitor cells. It was confirmed that the neural progenitor cells, unlike other neurons, may be cryopreserved, but may also be differentiated into the cholinergic neurons with high purity, unlike stem cells, for which the purity of differentiated cells is difficult to control. Producing the cholinergic neurons using such method is advantageous in that the cholinergic neurons can be differentiated from the neural progenitor cells, thereby enabling a more rapid production of the cholinergic neurons, in contrast to a conventional method for differentiating the cholinergic neurons from the stem cells. Additionally, it was also confirmed that when sonic hedgehog (SHH), known as a neuron differentiation inducer, is treated during an intermediate process of the neural progenitor cell production (process of obtaining neurospheres from the obtained embryoid bodies), a proportion of differentiation byproduct cells other than the cholinergic neurons differentiated from the neural progenitor cells significantly decreases, and therefore, an effect of an increase in efficiency of differentiation into the cholinergic neurons may be exhibited. Such effect was never reported in the conventional technique using known methods, and was confirmed by the present inventors for the first time.

An aspect of the present invention is to provide a method for producing cholinergic neurons, comprising obtaining neural progenitor cells from stem cells followed by differentiating the neural progenitor cells into cholinergic neurons.

As used herein, the term "stem cell" refers to a cell capable of differentiating into two or more new cells while having an ability to self-replicate. The stem cells can be divided into totipotent stem cells, pluripotent stem cells, and multipotent stem cells in accordance with differentiation potency, and into mesenchymal stein cells, embryonic stem cells, and induced pluripotent stem cells in accordance with the tissue from which the stem cells are derived.

In the present invention, the stem cells can be understood to be differentiated into the cholinergic neurons provided in the present invention, where the stem cells can be differentiated into the cholinergic neurons sequentially via embryoid bodies, rosettes, neurospheres, and neural progenitor cells. Therefore, in the present invention, if differentiation into the cholinergic neurons is possible, all types of stem cells such as mesenchymal stem cells, embryonic stem cells, and induced pluripotent stem cells, specifically, embryonic stem cells, induced pluripotent stem cells, or mesenchymal stem cells derived from bone marrow, adipose tissue, teeth, dental tissues, blood, umbilical cord blood, liver, skin, gastrointestinal tract, placenta, uterus, and fetus, can be used.

In a specific exemplary embodiment of the present invention, the induced pluripotent stem cells obtained by introducing hOct3/4-p53sh, hSox-KLF4, hUl, and EBNA1 genes into the skin fibroblasts were used as the stem cells for obtaining the cholinergic neuron production.

As used herein, the term "embryoid body", also known as a gemma cup, refers to a ball-like aggregate of the stem cells during early stages of cell division. The embryoid bodies exhibit similar pluripotency to conventional embryonic stem cells and thus can differentiate into bone cells, muscle cells, nerve cells, epithelial cells, fiber cells, and various other biological tissues.

In the present invention, the embryoid bodies can be used as an intermediate mediator for differentiating the stem cells into the neural progenitor cells, and can be obtained by culturing the stem cells in a conventional culture medium (e.g., DMEM/F12, KO-DMEM/F12, etc.) comprising various ingredients (e.g., blood serum, non-essential amino acids (NEAA), antibiotics, LDN193189, SB431542, etc.). Time for culturing to form the embryoid bodies from the stem cells is not particularly limited, but may be specifically 1 day to 10 days, more specifically 2 days to 7 days, and most specifically 4 days to 5 days.

In a specific exemplary embodiment of the present invention, the induced pluripotent stem cells were cultured for 4 days to 5 days to obtain the embryoid bodies.

As used herein, the term "neural progenitor cells", also known as "neuron precursor cells", broadly refers to all cells that can differentiate into neurons or exist in the differentiation process. Neural stem cells or other stem cells are differentiated to form neuroblasts, and the formed neuroblasts move to sites where neural tubes or neurons are formed, and are then morphologically and functionally differentiated to form axons and dendrites to ultimately form neurons. All cells undergoing differentiation, from stem cells until just before completion of differentiation, correspond to a wide range of the neural progenitor cells, whereas in a narrower range, neuroblasts that have completed differentiation correspond to the neural progenitor cells.

To obtain the neural progenitor cells from the embryoid bodies in vitro, the embryoid bodies are cultured in a culture medium for inducing neural differentiation (culture medium for forming rosettes) prepared by adding a differentiation-inducing factor such as sonic hedgehog (SHH) to a conventional culture medium for differentiating stem cells to obtain rosettes, and then the collected rosettes are cultured in the same culture medium for inducing neural differentiation to obtain the neurospheres, followed by culturing the neurospheres in a culture medium for neural progenitor cells.

Additionally, the culture medium for inducing neural differentiation refers to a culture medium in which the rosettes can be formed from the embryoid bodies, and the culture medium for inducing neural differentiation is not limited as long as the rosettes can be obtained by culturing the embryoid bodies, but may be specifically a culture medium comprising N2, B27, basic fibroblast growth factor (bFGF), and SHH, more specifically DMEM/F12 or KO-DMEM/F12 comprising N2, B27, bFGF, and SHH.

Additionally, the "culture medium for inducing neural differentiation" is mixed with the "culture medium for forming rosettes".

Additionally, the culture medium for neural progenitor cells in the present invention refers to a culture medium capable of forming the neural progenitor cells from the neurospheres. As long as the neural progenitor cells can be obtained by culturing the neurospheres therein, the culture medium for neural progenitor cells may be a serum-free medium, but is not limited thereto.

Additionally, time required for culturing to obtain the rosettes from the embryoid bodies is not particularly limited, but may be specifically 4 days to 10 days, more specifically 5 days to 9 days, and most specifically 7 days.

Additionally, time required for culturing to obtain the neurospheres from the rosettes is not particularly limited, but may be specifically 4 days to 10 days, more specifically 5 days to 9 days, and most specifically 7 days.

Therefore, time for culturing to obtain the neurospheres from the embryoid bodies using the culture medium for inducing neural differentiation comprising a neural differentiating-inducing component such as SHH is not particularly limited, but may be specifically 8 days to 20 days, more specifically 10 days to 18 days, and most specifically 14 days.

Specifically, obtaining the neurospheres may be a step to obtain the neurospheres by culturing the embryoid bodies in a culture medium for forming rosettes comprising N2, B27, basic fibroblast growth factor (bFGF), and SHH, followed by culturing the rosettes.

Additionally, time for culturing to obtain the neural progenitor cells from the neurospheres is not particularly limited, but may be specifically 1 day to 5 days, more specifically 1 day to 3 days, and most specifically 2 days.

As used herein, the term "rosette" refers to a cell aggregate obtained by culturing the embryoid bodies in the culture medium for inducing neural differentiation comprising a neuron differentiation-inducing component, where the cells are bonded in the form of a flower. The rosette can be understood as an intermediate cell in which a gene required for the differentiation from stem cells to neurons is expressed, thereby accompanying a morphological change. Additionally, accumulation of the rosettes is required to form the neurospheres from the rosettes more effectively, and therefore, it is preferable that as soon as the rosettes are formed, the rosettes are inoculated in a culture dish for high density and then cultured.

As used herein, the term "cholinergic neuron" refers to a neuron secreting acetylcholine as a chemical transmitter, and the cholinergic neurons located in the basal forebrain are called basal forebrain cholinergic neurons (BFCN). The cholinergic neurons are known to be directly involved in inducing nervous system diseases in animal brains and accompanied by damage to cholinergic neurons in the onset of various degenerative brain diseases such as Alzheimer's disease, Parkinson's disease, and amyotrophic lateral sclerosis. In particular, learning abilities, one of the main symptoms of Alzheimer's disease, is predicted to be caused by damage to cholinergic neurons.

In the present invention, the cholinergic neurons can be obtained by culturing the neural progenitor cells in the culture medium for differentiation into cholinergic neurons, and ingredients of the culture medium for differentiation into cholinergic neurons are not limited as long as the neural progenitor cells can be differentiated into the cholinergic neurons therein, but may specifically comprise a substance selected from the group consisting of glutamax, B27, EGF, heparin, ascorbic acid, brain-derived neurotrophic factor (BDNF), and a combination thereof.

Time required for differentiating the cholinergic neurons from the neural progenitor cells is not limited, but may be specifically 1 day to 10 days, more specifically 3 days to 7 days, and most specifically 5 days.

Further, when the cholinergic neurons are formed, neurons other than the cholinergic neurons may be formed from the neural progenitor cells as well. In order to prevent the formation of the other neurons, a differentiation inhibitor (e.g., AraC) may be added to inhibit differentiation into other neurons and proliferation thereof. Time required for treating the differentiation inhibitor is not particularly limited, but may be specifically 1 day to 5 days, more specifically 1 day to 3 days, and most specifically 2 days. The AraC refers to cytarabine.

Additionally, in order to promote the proliferation of the cholinergic neurons which are already formed, various growth factors (e.g., bFGF) can be added to a culture medium. Time for culturing with the growth factors in the culture medium is not particularly limited, but may be specifically 10 days to 30 days, more specifically 15 days to 25 days, and most specifically 20 days.

Therefore, specifically 4 days to 15 days, more specifically 6 days to 10 days, and most specifically 7 days after inoculating and culturing the neural progenitor cells into the culture medium for differentiation into cholinergic neurons, the proliferation of the cholinergic neurons can be promoted by adding the growth factors to the culture medium.

Using the method of the present invention can not only produce the cholinergic neurons with high purity, but also continuously produce the cholinergic neurons with the same traits using the neural progenitor cells that can be cryopreserved. This is advantageous in that by simply repeating the process of differentiating and producing the cholinergic neurons from the neural progenitor cells, time required for producing the cholinergic neurons can be shortened. In the case of using the cholinergic neurons produced in the present invention to treat Alzheimer's disease, cholinergic neurons that meet an in vivo condition of a patient must be used. Continuous transplantation of the cholinergic neurons may be required to be on a cycle depending on symptoms of the patient. In said case, if the cholinergic neurons first used and those subsequently used show different traits, there is a problem in that the chances of treating Alzheimer's disease may decrease sharply. However, as Alzheimer's disease requires long-term treatment, maintaining the first-used cholinergic neurons until the treatment is finished is known to be substantially impossible. Nonetheless, using the method provided in the present invention maintains the neural progenitor cells that can be differentiated into the cholinergic neurons and uses the neural progenitor cells to produce the cholinergic neurons of the same traits until treatment of patients with Alzheimer's disease is completed, thereby improving a treatment success rate of Alzheimer's disease significantly.

Additionally, there is an advantage in that by repeating the process of differentiating and producing the cholinergic neurons from neural progenitor cells which can be cryopreserved, time required for producing the cholinergic neurons can be shortened, compared to the conventional technique for cholinergic neuron production.

As a specific example of the method for producing the cholinergic neurons provided in the present invention, the method for producing the cholinergic neurons of the present invention may comprise:

(a) obtaining embryoid bodies by culturing the stem cells;

(b) obtaining neurospheres by culturing the embryoid bodies in a culture medium comprising Sonic Hedgehog (SHH);

(c) obtaining the neural progenitor cells by culturing the neurospheres; and (d) obtaining cholinergic neurons by culturing the neural progenitor cells in a culture medium for differentiation into cholinergic neurons, but is not limited thereto.

Additionally, in the present invention, step (b) may comprise obtaining rosettes by culturing the embryoid bodies in the culture medium comprising SHH, followed by obtaining the neurospheres by culturing the rosettes in the culture medium comprising SHH, but is not limited thereto.

Furthermore, step (d) in the present invention specifically may comprise:

(d1) producing the cholinergic neurons by culturing the neural progenitor cells in the culture medium for differentiation into cholinergic neurons;

(d2) inhibiting proliferation of neurons other than the cholinergic neurons by treating the culture medium with a differentiation inhibitor; and (d3) proliferating the cholinergic neurons by treating the culture medium with a growth factor, but is not limited thereto.

As described above, the stem cells of step (a) may be mesenchymal stem cells, embryonic stem cells, or induced pluripotent stem cells; the induced pluripotent stem cells may be obtained by introducing hOct3/4-p53sh, hSox-KLF4, hUl, and EBNA1 genes into the skin fibroblasts; the stem cells of step (a) may be cultured in DMEM/F12 comprising blood serum, non-essential amino acids (NEAA), antibiotics, LDN193189, and SB431542 to form the embryoid bodies; in step (b), the embryoid bodies are cultured while treating with SHH to obtain rosettes, and the rosettes are cultured while treating with SHH to obtain the neurospheres; the neurospheres obtained in step (c) may be cryopreserved and used in repeatedly reproducing the cholinergic neurons with the same traits; as the culture medium of step (d) for differentiating into the cholinergic neurons, KO-DMEM/F12 comprising glutamax, antibiotics, B27, EGF, and heparin; and by treating AraC and bFGF after the cholinergic neurons in step (d) are formed, the proliferation of neurons other than the cholinergic neurons can be inhibited and the cultured cholinergic neurons can be proliferated, respectively.

Figure 2:
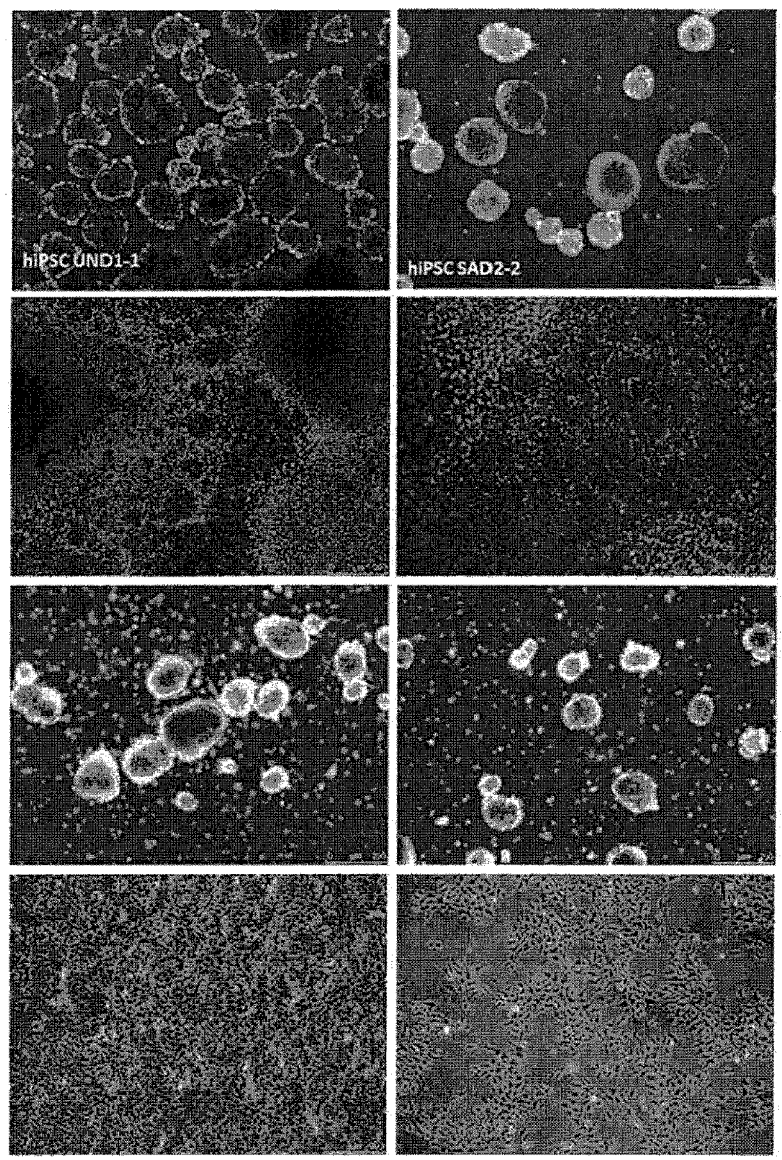
FIG. 2 is photomicrographs showing morphologies of the embryoid bodies, rosettes, neurospheres, and neural progenitor cells derived from skin fibroblasts obtained from a healthy subject and an Alzheimer's disease patient. The left images show the embryoid bodies, rosettes, neurospheres, and neural progenitor cells derived from skin fibroblasts obtained from the healthy subject, whereas the right images show the embryoid bodies, rosettes, neurospheres, and neural progenitor cells derived from skin fibroblasts obtained from the Alzheimer's disease patient.
Figure 3A:
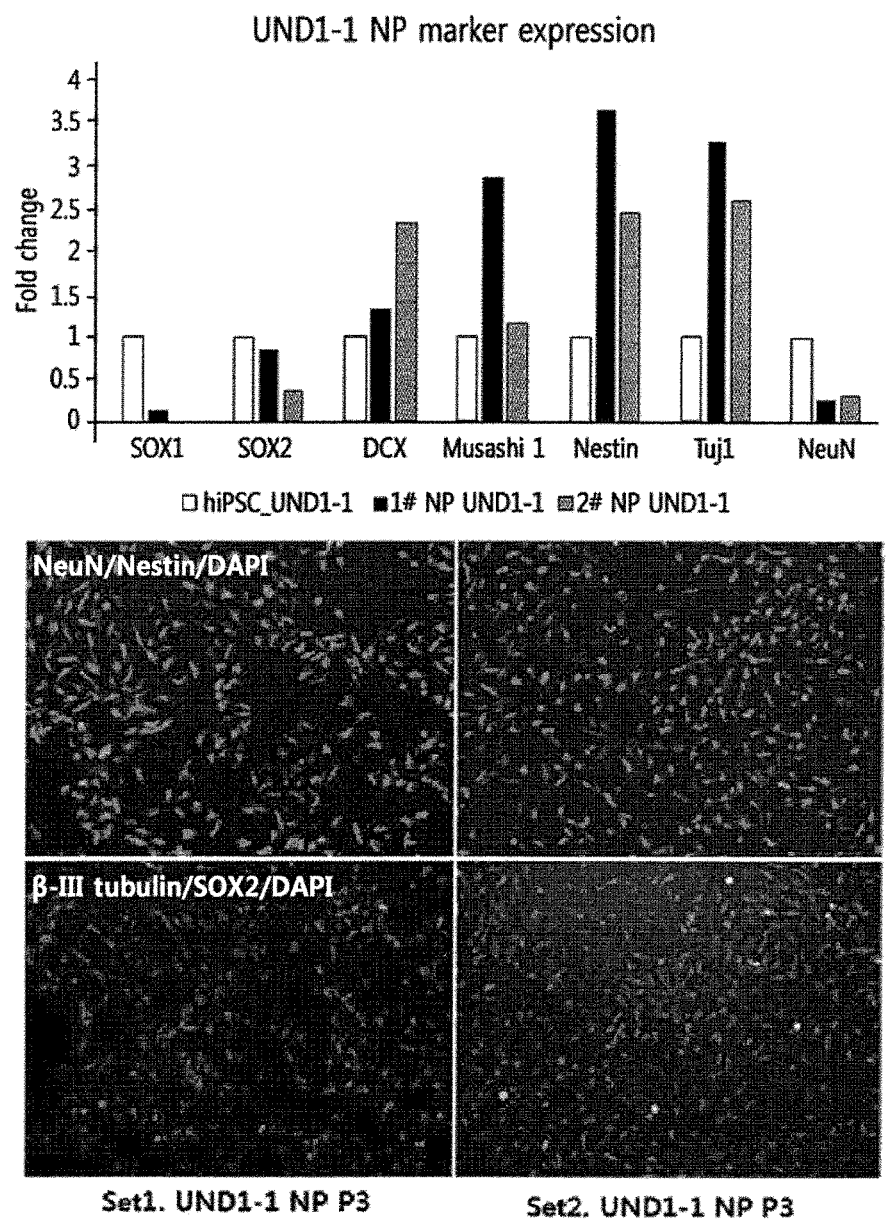
FIG. 3a is a graph and immunofluorescent stained images, showing a result of expression levels of markers of the neural progenitor cells for induced pluripotent stem cells (hiPSC_UND1-1) and neural progenitor cells (1#NP_UND1-1 and 2#NP_UND1-1) derived from skin fibroblasts obtained from the healthy subject using Q-PCR and immunofluorescent staining.
Figure 3B:
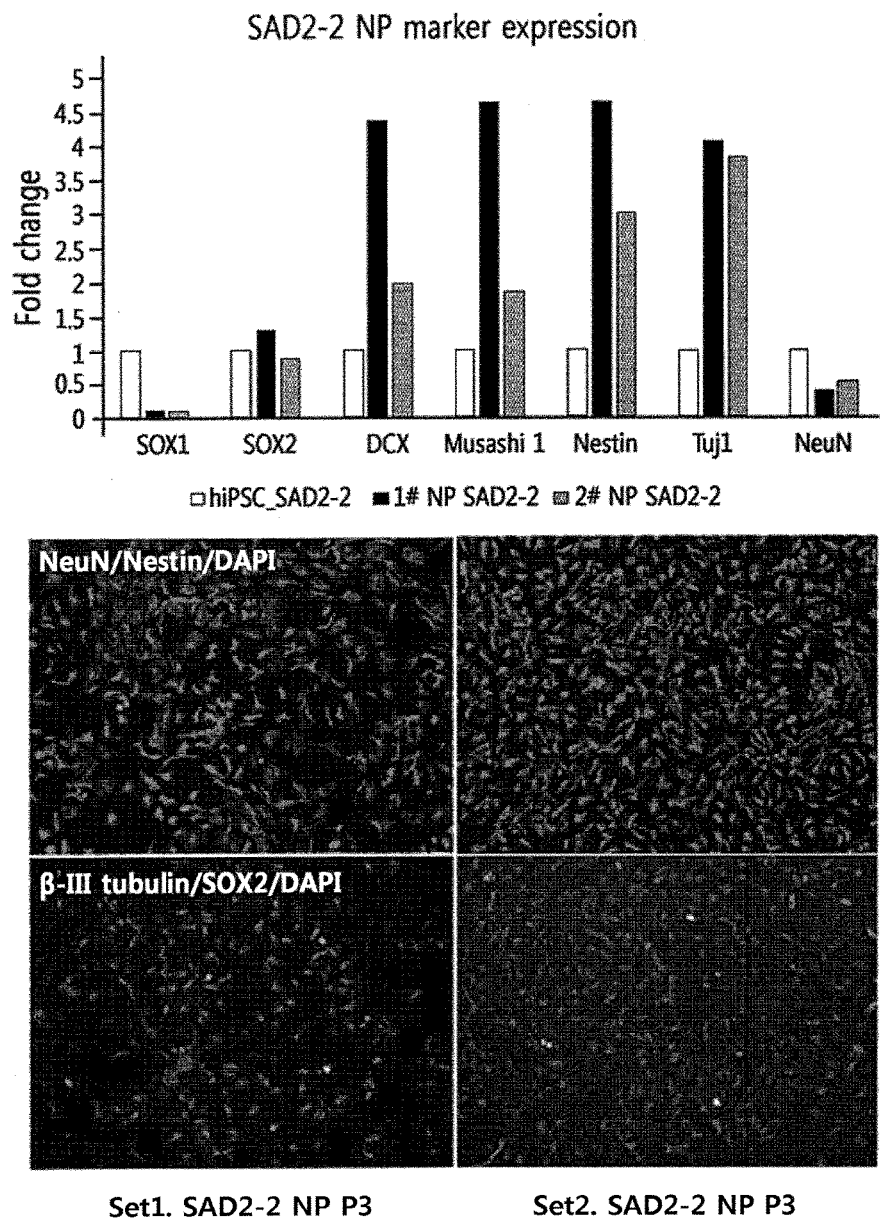
FIG. 3b is a graph and immunofluorescent stained images, showing a result of expression levels of markers of the neural progenitor cells for induced pluripotent stem cells (hiPSC_UND1-1) and neural progenitor cells (1#NP_UND1-1 and 2#NP_UND1-1) derived from skin fibroblasts obtained from the Alzheimer's disease patient using Q-PCR and immunofluorescent staining.
Figure 4:
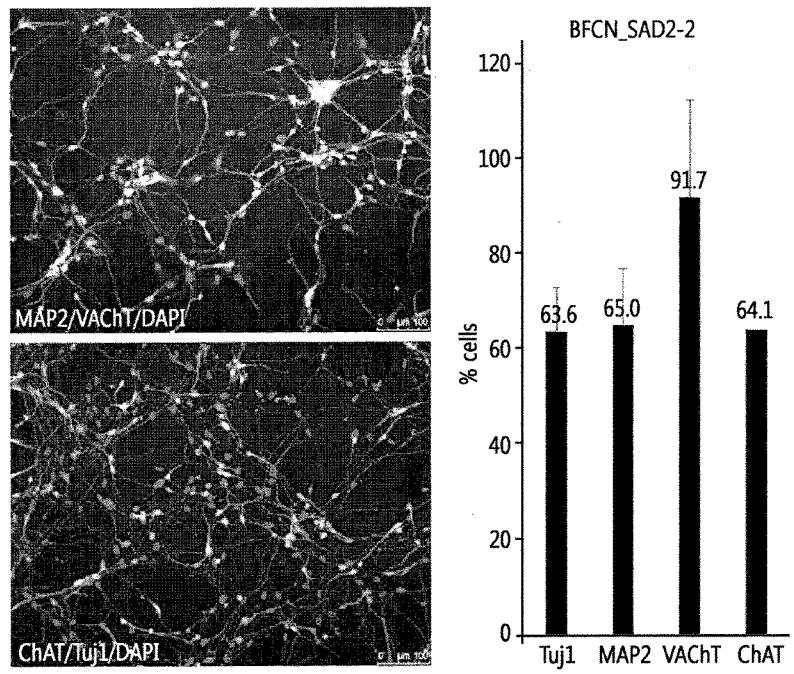
FIG. 4 is a graph and immunofluorescent stained images, showing a result of measurements of ratios of cells in which neuronal markers (Tuj1 and MAP2) are expressed and ratios of cells in which cholinergic neuron markers (VAChT and ChAT) are expressed, using the immunofluorescent staining for cholinergic neurons (BFCN_SAD2-2) obtained from skin fibroblasts obtained from Alzheimer's disease patients.
Figure 5:
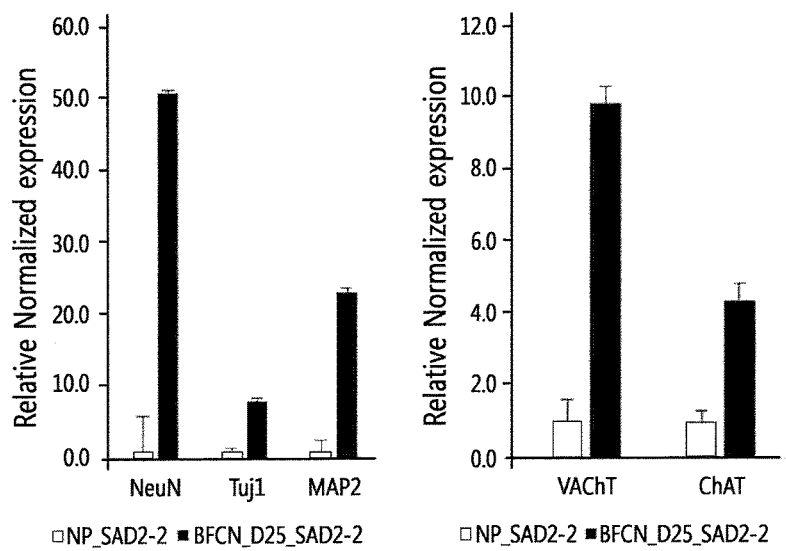
FIG. 5 is a graph showing comparative expression levels of neuronal markers (NeuN, Tuj1, and MAP2) and cholinergic neuron markers (VAChT and ChAT) for neural progenitor cells (NP_SAD2-2) and the cholinergic neurons (BFCN_D25_SAD2-2) derived from Alzheimer's disease patients.

According to a specific exemplary example of the present invention, the skin fibroblasts are used to obtain the induced pluripotent stem cells, and the induced pluripotent stem cells are cultured to obtain the embryoid bodies. The embryoid bodies are cultured to obtain rosettes, and the rosettes are collected and then cultured again to obtain the neurospheres (FIGS. 2 and 3). The neurospheres are cultured in the culture medium for differentiation into cholinergic neurons to produce the cholinergic neurons (FIGS. 4 and 5).

Figure 6:
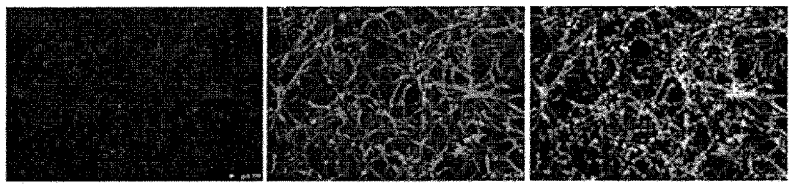
FIG. 6 is a graph and immunofluorescent stained image, showing comparative expression levels of the neuronal markers, the cholinergic markers (MAP2 and Tuj1), and GABAergic neuron marker (GABA) for cholinergic neurons derived from Alzheimer's disease patients.
Figure 6:
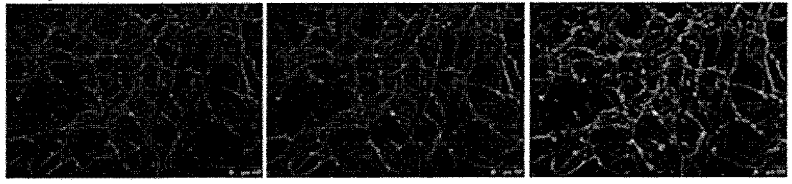
Figure 6:
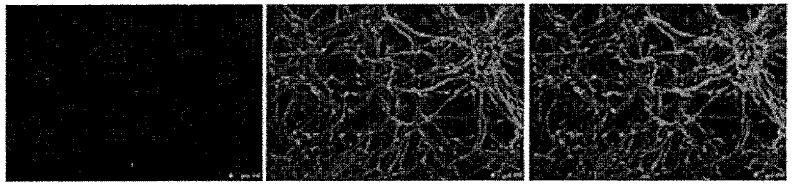
Figure 6:
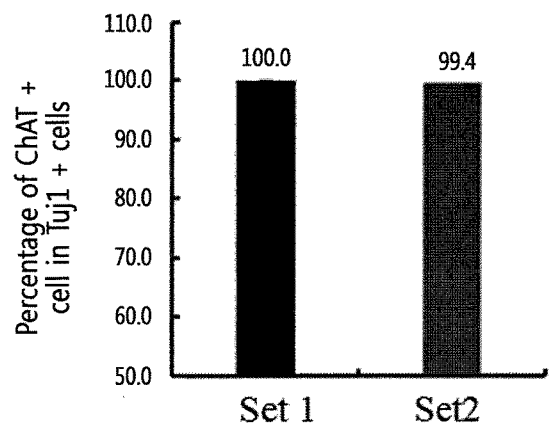

Additionally, in a specific exemplary example of the present invention, 99.4% or 100 of the differentiated neurons were confirmed to be cholinergic neurons, indicating that the cholinergic neurons with the same traits can be produced with high purity (FIG. 6).

Another aspect of the present invention is to provide the cholinergic neurons produced by the method for preparing the cholinergic neurons described above.

The cholinergic neurons provided in the present invention contain other cells excluding the cholinergic neurons in a significantly low amount, compared to the cholinergic neurons produced by the conventional preparation method, thereby significantly increasing purity of the cholinergic neurons. The cholinergic neurons of the present invention can improve therapeutic efficiency of patients with a disease that require transplantation of the cholinergic neurons such as Alzheimer's disease.

MODE FOR INVENTION

Hereinbelow, the present invention will be described in detail with accompanying exemplary embodiments. However, the exemplary embodiments disclosed herein are only for describing the invention more specifically and should not be construed as limiting the scope of the present invention.

Example 1: Obtaining of Induced Pluripotent Stem Cells (iPSC)

Each skin fibroblast (AG06263, AG06264, AG07871, and AG07926; Coriell) obtained from healthy subjects and Alzheimer's disease patients is cultured, and hOct3/4-p53sh, hSox-KLF4, hUl, and EBNA1 are introduced therein using Neon™ transfection system (MPK10096, Invitrogen) to obtain transformants. After saturating the obtained transformants to a level of 80%, it was inoculated into a culture dish coated with matrigel (47743-720, Corning) and subcultured to obtain induced pluripotent stem cells. The culture medium used herein was mTeSR™ 1 (05850, Stem Cell™ technologies) comprising 50 ng/mL bFGF, 3 uM CCHIR99021 (13122-1, Cayman), 0.5 uM A83-01(sc-203791, Santa Cruz), 0.2 mM sodium butyrate, and 1 mM nicotinamide. After cutting the cells saturated and cultured during the subculture, collagenase IV was treated to separate the cells.

Example 2: Production of Cholinergic Neurons

The cholinergic neurons were produced by differentiating each iPSC obtained in Example 1.

Example 2-1: Obtaining of Embryoid Bodies

After cutting the iPSCs into a size of about 150 collagenase IV was treated to separate the cells, and the separated cells were washed with DMEM/F12 (11330, Gibco). The washed iPSCs were inoculated into a culture medium for differentiation into embryoid bodies (80% DMEM/F12, 20% serum replacement, and 1% NEAA (11140-050, Gibco), 1% penicillin/streptomycin, 100 nM LDN193189 (S2618, Selleckchem), and 10 μM SB431542 (301836-41-9, ABcam)), and cultured for 4 days to 5 days to obtain the embryoid bodies.

Example 2-2: Obtaining of Rosettes and Neurospheres

The culture medium in which the embryoid bodies obtained from Example 2-1 were formed was left to stand to precipitate the embryoid bodies, and the culture medium was removed to recover the embryoid bodies. The recovered embryoid bodies were added to a culture dish coated with matrigel along with the culture medium for forming rosettes (DMEM/F12, 1% N2 (gib-17502-048, Gibco), 1% B27 (17504044, Gibco), 20 nM bFGF, 50 ng/mL, SHH (1845-sh-100/cf, R&D)), and then cultured for 7 days to obtain rosettes.

The obtained rosettes were collected and introduced in a culture medium for forming rosettes, and then cultured for 7 days to obtain the neurospheres.

Example 2-3: Obtaining of Neural Progenitor Cells

The neurospheres obtained from Example 2-2 were washed with PBS and treated with accutase to isolate single cells, and then washed with a culture medium comprising FBS. The washed single cells were cultured with Stemdiff™ Neural Progenitor culture medium (05833, Stem Cell™ Technologies) in a culture dish coated with matrigel for 2 days to obtain the neural progenitor cells. The neural progenitor cells were treated with trypsin to isolate single cells, and were then subcultured with Stemdiff™ Neural Progenitor culture medium in a culture dish coated with matrigel (FIG. 2).

FIG. 2 is photomicrographs showing morphologies of the embryoid bodies, rosettes, neurospheres, and neural progenitor cells derived from skin fibroblasts obtained from a healthy subject and an Alzheimer's disease patient. The left images show the embryoid bodies, rosettes, neurospheres, and neural progenitor cells derived from skin fibroblasts obtained from the healthy subject, whereas the right images show the embryoid bodies, rosettes, neurospheres, and neural progenitor cells derived from skin fibroblasts obtained from the Alzheimer's disease patient. As shown in FIG. 2, the embryoid bodies, rosettes, neurospheres, and neural progenitor cells derived from skin fibroblasts of the healthy subject and those of the Alzheimer's disease patient are morphologically identical.

Example 2-4: Production of Cholinergic Neurons

The subcultured neural progenitor cells in Example 2-3 were cultured with a culture medium for differentiation into cholinergic neurons (i.e., KO-DMEM/F12 with a ratio of 7:3, comprising 2 mM Glutamax (35050-061, Gibco), 1% penicillin/streptomycin, 1% B27, 20 ng/mL EGF (GF144, Millipore), and 5 μg/mL heparin (h3393, Sigma)) in a culture dish coated with poly-D-lysine/laminin (#40210, #40232, Collaborative Research) for 5 days. The culture medium was treated with 2.4 μM AraC (C1768, Sigma) for 2 days, and then with 10 ng/mL bFGF for 23 days to differentiate the neural progenitor cells into the cholinergic neurons to eventually to produce the cholinergic neurons.

Example 3: Cholinergic Neuron Differentiation Results and Verification

Example 3-1: Expression Level of Differentiation Markers in Stem Cells and Neural Progenitor Cells During the differentiation into cholinergic neurons using the method of Example 2, the iPSCs and neural progenitor cells were each obtained, and an expression level of neural progenitor cell marker proteins expressed in each cell was confirmed.

Each of the iPSCs and neural progenitor cells was treated with trizol (TRI Reagent solution, Ambion, am9738), and total RNA of each cell was obtained. cDNA was synthesized by performing a method of using reverse transcriptase (M-MLV reverse transcriptase (M1701, Promega)) on the obtained total RNA. By performing a method of using SYBR Premix Ex Taq II (Takara, RR820A) on the obtained cDNA, expression levels of SOX1 and SOX2, stem cell markers; DCX, Musashil, Nestin, and Tuj1, neural progenitor cell markers; and NeuN, a neuronal marker, were compared. Additionally, immunofluorescent staining for NeuN, Nestin, and SOX2 was performed (FIGS. 3a and 3b). At this time, β-III tubulin was used as an internal control group.

As shown in FIGS. 3a and 3b, it was confirmed that expression levels of all marker proteins in the iPSCs obtained from the skin fibroblasts of healthy subjects and Alzheimer's disease patients were uniformly expressed. In contrast, it was found that expression levels of the stem cell markers (SOX1 and SOX2) as well as the neuronal marker (NeuN) were low in the neural progenitor cells, whereas the neural progenitor cell markers (DCX, Musashil, Nestin, and Tuj1) showed a significantly high expression level.

Therefore, each of the neural progenitor cells obtained in Example 2 was found to be normally differentiated neural progenitor cells.

Example 3-2: Expression Level of Differentiation Markers in Cholinergic Neurons

Immunofluorescent staining for neuronal markers (Tuj1 and MAP2) and cholinergic neuron markers (VAChT and ChAT) was performed on the cholinergic neurons (BFCN-_SAD2-2) derived from Alzheimer's disease patients to compare expression levels thereof (FIG. 4).

As shown in FIG. 4, it was found that Tuj1 and MAP2, which are neuronal markers, were expressed in about 63% to 65% of cells, whereas VAChT, the cholinergic neuron marker, was expressed in about 91.7% of cells. Accordingly, it was confirmed that most of the cells differentiated from the iPSC derived from the Alzheimer's disease patient were the cholinergic neurons.

Additionally, relative expression levels of the neuronal markers (NeuN, Tuj1, and MAP2) and cholinergic neuron markers (VAChT and ChAT) were compared on the neural progenitor cells (NP_SAD2-2) and cholinergic neurons (BFCN_D25_SAD2-2) derived from the Alzheimer's disease patients, obtained using the method of Example 2 (FIG. 5).

As shown in FIG. 5, in the neural progenitor cells (NP_SAD2-2), all neuronal markers (NeuN, Tuj1, and MAP2) and cholinergic neuron markers (VAChT and ChAT) were expressed at a relatively low level. In contrast, in the cholinergic neurons (BFCN_D25_SAD2-2), not only the cholinergic markers (VAChT and ChAT) but also the neuronal markers (NeuN, Tuj1, and MAP2) were expressed at a high level.

Therefore, the cells ultimately differentiated by the method of Example 2 were confirmed again to be the cholinergic neurons.

Additionally, relative expression levels of the neuronal markers (MAP2 and Tuj1), cholinergic neuron markers (VAChT and ChAT), and GABAergic neuron marker (GABA) were compared on the neural progenitor cells (BFCN_D25_SAD2-2) derived from the Alzheimer's disease patients, obtained using the method of Example 2 (FIG. 6).

As shown in FIG. 6, most cells in the cells stained with MAP2 or Tuj1 were stained with VAChT or ChAT, but not with the GABAergic neuron marker.

Furthermore, as a result of quantifying the results of the above immunostaining, it was confirmed that a proportion of ChAT-positive cells was about 99.4% or 100% in Tuj1-positive cells which are neuronal markers.

Accordingly, it was found that cholinergic neurons with the same traits can be produced with very high purity by using the method for producing cholinergic neurons provided in the present invention.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

What is claimed is:

1. A method for preparing cholinergic neurons comprising a step of forming neural progenitor cells from stem cells, followed by differentiating the neural progenitor cells into cholinergic neurons wherein the method comprises:
    (a) obtaining embryoid bodies by culturing the stem cells;
    (b) obtaining neurospheres by culturing the embryoid bodies in a culture medium comprising Sonic Hedgehog (SHH);
    (c) obtaining the neural progenitor cells by culturing the neurospheres; and
    (d) obtaining cholinergic neurons by culturing the neural progenitor cells in a culture medium for differentiation into cholinergic neurons.

2. The method of claim 1, wherein the stem cells are mesenchymal stem cells, embryonic stem cells, or induced pluripotent stem cells.

3. The method of claim 2, wherein the induced pluripotent stem cells are obtained by introducing hOct3/4-p53sh, hSox-KLF4, hUl, and EBNA1 genes into skin fibroblasts.

4. The method of claim 1, wherein the stem cells are differentiated into the cholinergic neurons sequentially via embryoid bodies, rosettes, neurospheres, and neural progenitor cells.

5. The method of claim 1, wherein step (a) is to culture the stem cells in DMEM/F12 or KO-DMEM/F12.

6. The method of claim 1, wherein step (b) is performed for 8 days to 20 days.

7. The method of claim 1, wherein step (b) is to obtain the neurospheres by culturing the embryoid bodies in a culture medium for forming rosettes comprising N2, B27, basic fibroblast growth factor (bFGF), and SHH to obtain rosettes, followed by culturing the rosettes.

8. The method of claim 7, wherein the culture medium for forming rosettes is DMEM/F12 or KO-DMEM/F12 comprising N2, B27, bFGF, and SHH.

9. The method of claim 1, wherein step (c) is to obtain the neural progenitor cells by culturing the neurospheres in a serum-free culture medium.

10. The method of claim 1, wherein the culture medium for differentiation of cholinergic neurons in step (d) comprises a substance selected from the group consisting of EGF, heparin, ascorbic acid, brain-derived neurotrophic factor (BDNF), and a combination thereof.

11. The method of claim 1, wherein step (d) comprises:
    (d1) producing the cholinergic neurons by culturing the neural progenitor cells in the culture medium for differentiation of cholinergic neurons;
    (d2) inhibiting proliferation of neurons other than the cholinergic neurons by treating the Culture medium with a differentiation inhibitor; and
    (d3) proliferating the cholinergic neurons by treating the culture medium with a growth factor.

12. The method of claim 11, wherein step (d2) is performed for 1 day to 5 days, and the differentiation inhibitor comprises cytarabine (AraC).

13. The method of claim 11, wherein step (d3) is performed 4 days to 15 days after the initiation of step (d), and the growth factor comprises bFGF.

14. The method of claim 1, wherein the method comprises:
    (a') obtaining embryoid bodies by culturing the stem cells for 1 day to 10 days;
    (b') obtaining rosettes by culturing the embryoid bodies for 4 days to 10 days while treating with SHH;
    (c') obtaining neurospheres by culturing the rosettes for 4 days to 10 days while treating with SHH;
    (d') obtaining the neural progenitor cells by culturing the neurospheres for 1 day to 5 days;
    (e') obtaining the cholinergic neurons culturing the neural progenitor cells for 3 days to 10 days;
    (f') inhibiting proliferation of neurons other than the cholinergic neurons by treating the medium of step (e') with cytarabine and culturing the cytarabine-treated medium for 1 day to 5 days; and
    (g') proliferating the cholinergic neurons by treating the medium with bFGF and culturing the bFGF-treated medium for 10 days to 30 days.

* * * * *